(12) United States Patent
Boardman (10) Patent No.: US 9,146,208 B2
(45) Date of Patent: Sep. 29, 2015

(54) LEAD-FREE OXYGEN SENSOR

(71) Applicant: Alan Boardman, Holladay, UT (US)

(72) Inventor: Alan Boardman, Holladay, UT (US)

(73) Assignee: Brigham Young University, Provo, UT (US)

( * ) Notice: Subject to any disclaimer, the term of this patent is extended or adjusted under 35 U.S.C. 154(b) by 151 days.

(21) Appl. No.: 13/630,550

(22) Filed: Sep. 28, 2012

(65) Prior Publication Data

US 2014/0090977 A1    Apr. 3, 2014

Related U.S. Application Data

(60) Provisional application No. 61/541,009, filed on Sep. 29, 2011.

(51) Int. Cl.
*G01N 27/413*    (2006.01)
*G01N 27/404*    (2006.01)
*G01N 27/30*    (2006.01)

(52) U.S. Cl.
CPC ............ *G01N 27/304* (2013.01); *G01N 27/404* (2013.01); *G01N 27/413* (2013.01)

(58) Field of Classification Search
CPC . G01N 27/304; G01N 27/404; G01N 27/413; G01N 27/431
USPC .......................... 204/421–429, 400, 415, 431
See application file for complete search history.

(56) References Cited

U.S. PATENT DOCUMENTS

| | | | | |
|---|---|---|---|---|
| 3,616,416 A * | 10/1971 | Linenberg et al. | ............ | 204/409 |
| 4,132,616 A * | 1/1979 | Tantram et al. | ............... | 204/415 |
| 4,252,627 A * | 2/1981 | Ohashi et al. | ................. | 204/415 |
| 5,686,205 A * | 11/1997 | Bai | ............. | 429/218.1 |
| 6,130,004 A * | 10/2000 | Li et al. | ...................... | 429/218.1 |
| 7,052,802 B2 * | 5/2006 | Tsukamoto et al. | ........ | 429/231.7 |
| 7,664,607 B2 * | 2/2010 | Broy | ............................... | 702/24 |
| 2003/0048594 A1 * | 3/2003 | Shinozaki et al. | ............ | 361/502 |
| 2010/0104934 A1 * | 4/2010 | Visco et al. | .................... | 429/105 |
| 2011/0076556 A1 * | 3/2011 | Karthikeyan et al. | ......... | 429/188 |
| 2011/0177413 A1 * | 7/2011 | Tao et al. | ....................... | 429/429 |
| 2013/0059176 A1 * | 3/2013 | Stefani et al. | ................... | 429/50 |

FOREIGN PATENT DOCUMENTS

| | | | |
|---|---|---|---|
| WO | WO2011/113429 | * | 9/2011 |
| WO | WO2011/137239 | * | 11/2011 |
| WO | WO 2013/039414 | * | 3/2013 |

OTHER PUBLICATIONS

Raj et al. (Journal of Applied Electrochemistry 23 (1993) 728-734).*

* cited by examiner

*Primary Examiner* — Jennifer Dieterle
(74) *Attorney, Agent, or Firm* — Dax D. Anderson; Kirton McConkie (57) ABSTRACT

An electrochemical sensor cell is disclosed. The cell comprised of a diffusion membrane, a cathode, an anode, an electrolyte, electronic circuit board with electronic leads contained in housing. The anode is made of substantially pure bismuth. The electrolyte may be either solid or aqueous solution of potassium hydroxide (KOH) solution or acetic acid ($CH_3COOH$). The cathode may be a carbon fiber substrate with gold deposited thereon. The sensor may be RoHS compliant.

19 Claims, 5 Drawing Sheets

LEAD-FREE OXYGEN SENSOR

RELATED APPLICATIONS

This application claims priority to U.S. Provisional Patent Application No. 61/541,009, filed Sep. 29, 2011, entitled "Lead-Free Oxygen Sensor and Systems and Methods Therefore

BACKGROUND

Background of the Invention and Related Art

Electrochemical cells are devices that have been used in various industries and applications such as Medical, Mining, Landfill, Oil, and Scuba for over many decades. An electrochemical cell converts chemical energy into electrical energy through the processes of oxidation and reduction. One of the primary uses of galvanic electrochemical cells has been used in the medical industry to detect the percentage of oxygen being administered to a patient. Common medical uses include the treatment of chronic obstructed pulmonary disease through the use of oxygen ventilators, continuous positive airway pressure (CPAP) treatment for sleep apnea, spot checking oxygen concentrators, air/O2 gas blending systems, and anesthesia gas delivery systems. The electrochemical cell is an integral part of these machines. Electrochemical cells provide an electrical output to the equipment that is directly proportional to the percentage of oxygen in the environment.

Electrochemical cells are constructed with a gas permeable diffusion membrane, an anode, a cathode, electrochemical electrolyte solution, outer housing, containment components, and electronic circuit board.

The output of the electrochemical cell is a current most commonly in microamperes ($\mu A$). The current is generated as electrons pass from the oxidation process at the anode and the diffusion of ions into the electrolyte solution from the oxygen reduction process at the cathode as per Faraday's Laws of electrolysis. The current is passed through a resistive circuit to convert the current (I) to a voltage output. Voltage output (current output) is directly proportional to the percentage of O2 in the environment and as such, medical equipment can sense and changes in voltage output and calculate the change in O2 percentage.

The electrochemical process is well known as is briefly described as follows:

Oxygen molecules diffuse through the diffusion membrane of the cell and a reduction process occurs in a cell at the area where a triple phase boundary is present. The diffusion membrane is typically from the fluorinated polymer family known as the trade name Teflon®. These are comprised of Polytetrafluoroethylene and Fluorinated Ethylene Propylene, and Tetrafluoroethylene films. This is where the O2 (g), the Ca(s) and the electrolyte (l) are in simultaneous contact with each other. Ca stands for catalyst material. The general reduction reaction can be described by the Kröger-Vink Notation.

$$\frac{1}{2}O_2\ (g) + S_{(ed)} \rightarrow O_{ad(ed)} \quad \text{(Eq. 1a)}$$

$$O_{ad} + V_{o(el)} \rightarrow 2h + O^x_{o(el)} + s_{(ed)} \quad \text{(Eq. 1b)}$$

(0) is the oxygen gas, s refers to the cathode active site surface, and (ed) refers to the cathode, typically made of gold, platinum, or another highly active metal. (el) refers to the electrolyte solution which is a potassium hydroxide (KOH) solution or an acetic acid (CH3COOH) solution.

An electrochemical reaction at the anode is an oxidation process as follows:

$$2Me + 4OH^- \rightarrow 2MeO_2 + 2H_2O + 4e^- \quad \text{(Eq. 2a)}$$

$$2Me \rightarrow 2Me^{2+} + 4e^- \quad \text{(Eq. 2b)}$$

(Me) stands for the anode metal before and after oxidation as well as any metallic oxide state that may exist after the process.

SUMMARY AND OBJECTS OF THE INVENTION

An electrochemical sensor that ascertains the concentration of oxygen as a percentage the gas flowing across the diffusion membrane. A electrochemical oxygen sensor comprises an anode, a cathode, a diffusion membrane, an electrolyte that may comprise either a solution in a housing and containing an electronic circuit board with a resistive circuit and electrical leads. The anode comprises substantially pure bismuth.

An RoHS compliant electrochemical oxygen cell for the various industries that utilize such technology.

The electrochemical sensor comprises a lead-free anode material, may be made from pure bismuth. The bismuth anode has the ability to directly replace a lead anode, a non RoHS compliant material, in current cells which utilize standard electrolytes thus not requiring special additives or agents not already known to the field. The embodiment is comprised of current design aspects of an electrochemical cell comprised of the diffusion membrane with a cathode, the anode (bismuth), an electrolyte, an outer housing and containment parts, an electronic circuit and electronic leads.

The cathode may comprise a carbon fiber sheet with gold deposited on the surface and/or within the carbon fibers.

The sensor may comprise an electrochemical cell further comprising a substantially pure bismuth anode. In certain embodiments a nickel wire that is coiled or pig-tailed and encapsulated within substantially pure bismuth. Alternatively, the nickel may encapsulate a substantially pure bismuth core to function as an anode.

The sensor further comprises a diffusion membrane having chemically resistive oxygen permeable polymer film. The membrane may further comprise a fluorinated polymer film. A surface of the film may be covered with gold to act as a catalyst. The gold may be adsorbed to the surface of the film by deposition techniques, evaporative techniques, lamination techniques, pulse laser techniques, chemical vapor deposition techniques and other physical deposition techniques known in the art.

The electrolyte solution may comprise a potassium hydroxide solution, an acetic acid with potassium acetate where said solution is approximately 6.0 molar solution or other electrolytes commonly known in the art. Alternatively the electrolyte may be a solid electrolyte commonly known in the art.

The cell further comprises a metallic retaining screen often in the shape of a disk. The screen generally comprises a stainless steel or titanium substrate. The screen is also perforated.

A gold plated titanium electrical connection wire is spot welded to the screen. However, the wire may be constructed of nickel, or other non-corrosive and/or chemically resistant electron-conducting material to conduct electrons from the cathode to the electronic circuit board.

In certain embodiments the electronic circuit board comprises resistors, thermistors, and electrical connection leads. Alternatively, the electrical connection wire may be connected to instrumentation to allow the collection of data.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE PREFERRED EMBODIMENTS

This specification describes exemplary embodiments and applications of the invention. The invention, however, is not limited to these exemplary embodiments and applications or to the manner in which the exemplary embodiments and applications operate or are described herein. Moreover, the Figures may show simplified or partial views, and the dimensions of elements in the Figures may be exaggerated or otherwise not in proportion for clarity. In addition, as the terms "on," "attached to," or "coupled to" are used herein, one object (e.g., a material, a layer, a substrate, etc.) can be "on," "attached to," or "coupled to" another object regardless of whether the one object is directly on, attached, or coupled to the other object or there are one or more intervening objects between the one object and the other object. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "ones" means more than one.

DESCRIPTION OF THE REFERENCE NUMBERS USED IN FIGS. 1-2

Figure 1:
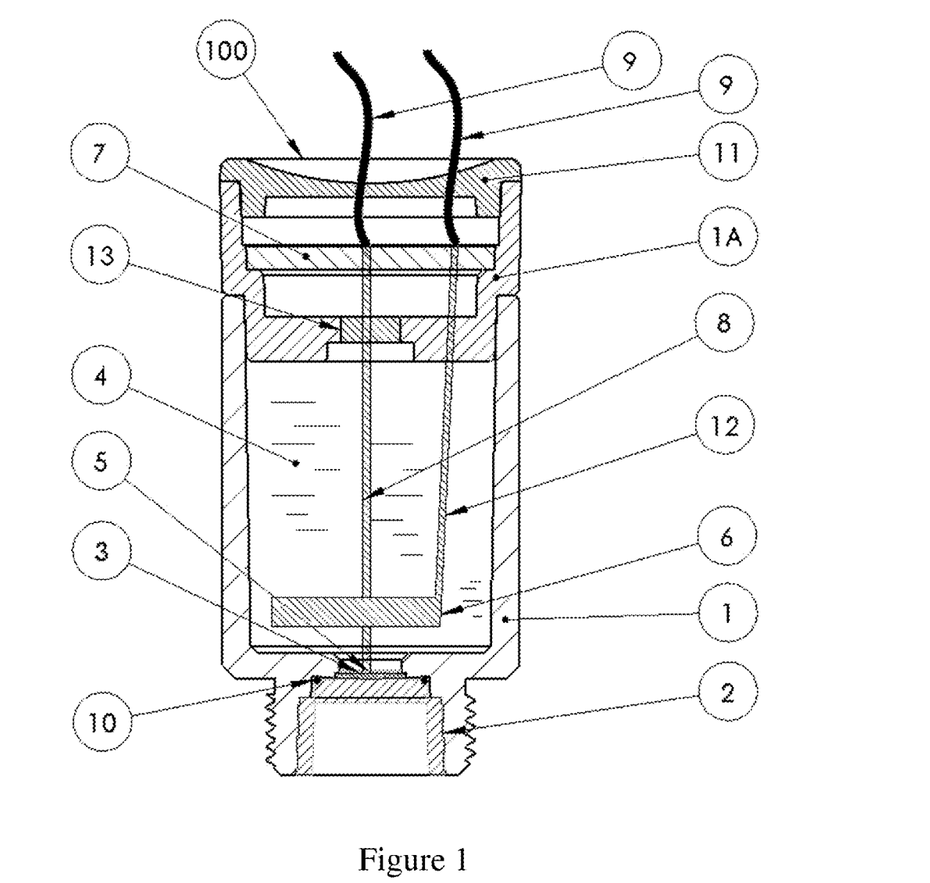
FIG. 1 is a cross section illustration of an electrochemical cell according to the certain exemplary embodiments.
Figure 2:
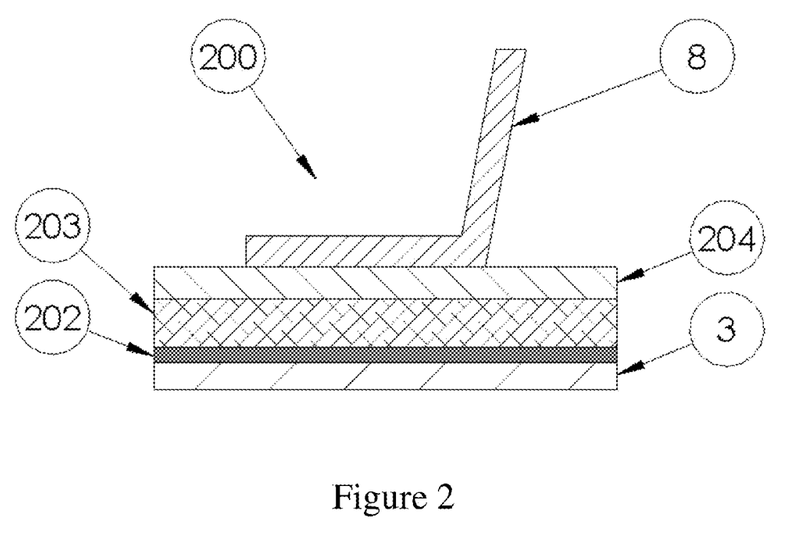
FIG. 2 is an illustration of the carbon fiber cathode assembly with the diffusion membrane.

100 Electrochemical cell
1 Outer Cell Housing
1a Outer Cell Housing Containment Base Plate
2 Cell Diffusion and Cathode Assembly Retaining Component
3 Diffusion Membrane
4 Electrolyte Solution
5 Cathode Assembly
6 Bismuth Anode
7 Electronic Circuit Board
8 Cathode Electrical Lead Wire
9 Cell Electrical Lead
10 O-Ring
11 End Cap
12 Nickel Wire Lead
200 Cathode and diffusion membrane assembly
5 Diffusion Membrane (Also referenced in FIG. 1.)
202 Deposited Metal
203 Carbon Fiber Sheet
204 Metal Retaining Screen Disk Referring to FIGS. 1 and 2, an electrochemical cell 100 comprising an outer cell housing 1 made from CPVC or other chemically resistant material. The cell 100 further comprises a containment base plate 1a that seals the cavity inside the cell. A cell diffusion membrane and cathode assembly retaining component 2 is coupled to the outer cell housing 1 to secure the retaining component 2 to the outer cell housing. A diffusion membrane 3 and cathode assembly 5 are secured by the retaining assembly 2 on one side and the outer cell housing 1 on the other side of the membrane 3 and assembly 5. The housing 1 and retaining assembly 2 sandwich the diffusion membrane 3 and cathode assembly 5. The cavity of the cell 100 is filled with an electrolyte solution 4 which drives the reduction oxidation reaction. The cathode assembly 5 may comprise gold, platinum, gold deposited on carbon fiber or other highly reactive materials.

The anode 6 comprises a substantially pure bismuth metal.

The cell 100 may further comprise an electronic circuit board 7 or instrumentation may be coupled to the cell electrical leads 9 to measure the current generated by the cell 100. Alternatively, a resistive circuit board 7 will provide the cell's 100 voltage output. The cell 100 further comprises an electrical lead wire 8 from the cathode assembly to the electronic circuit board 7 or alternatively directly to instrumentation. The o-ring 10 seals the edge of the film 3 to prevent electrolyte 4 from leaking around the edge of the film 3. Moreover, seating the o-ring 10 stretches the film 3 to remove wrinkles or other unevenness to ensure consistent and constant diffusion across the membrane 3 surface. The end cap 11 is coupled to the outer housing base plate 1a to enclose and protect a circuit board 7 within the outer house base plate 1a. The cell further comprises a nickel wire lead 12 encapsulated by or encapsulating bismuth anode 6 and electrically coupling the anode 6 to the circuit board 7 or alternatively to instrumentation.

Diffusion membrane and cathode assembly 200 comprises the diffusion membrane 3 and a deposited metal layer 202 where the layer 202 can be deposited on the membrane 3 surface closest to the electrolyte 4. The metal layer 202 can also be deposited on the carbon layer 203 such as a carbon fiber sheet.

A metal retaining screen 204 both retains the membrane 3 and carbon fiber 203 and gold layer 202 in the front of the outer cell housing 1 and the screen 204 acts as the electron collector and conductor, being connected to the cathode lead wire 8.

In the cell, 100 the membrane 5 controls the diffusion rate of the oxygen gas across the cell membrane 5 by the diffusion properties and thickness of the material as is commonly known in the art. Other methods of controlling diffusion rates may further comprise laser-drilled pores and other techniques commonly known in the art.

In one exemplary embodiment the cell anode 6 referenced in FIG. 1 is fabricated of substantially pure bismuth. An exemplary amount of substantially pure bismuth is 99.997% pure bismuth granules. The exemplary embodiment teaches a bismuth anode 6 manufactured using a casting technique. In one embodiment the anode 6 comprises bismuth of approximate weight of 5 grams where the granules are melted and a 0.010 inch diameter (30 gage) nickel wire 12 can be coiled and encapsulated within the bismuth melt with 3 inches of nickel wire 12 remaining out of the melt. A cast anodes 6 may further be allowed to cool at room temperature to form a disk anode 6 or any other appropriate shape, and size to function in the inner cavity of the cell 100. The dimensions referenced here or in any other embodiment may are representative only and unless otherwise stated, should be understood to be functional with the electrochemical cell 100.

Another exemplary embodiment of the electrochemical cell 100 is a cell anode 6 made of pure bismuth fabricated with a press technique where 99.997% pure bismuth granules of approximate weight of 5 grams were pressed with a high pressure press around and encapsulating a 0.010 inch diameter (30 gage) nickel coiled wire 12 into a flat bar of approximately 0.25 inch×0.125 inch cross section and 0.75 inch in length with 3 inches of nickel wire 12 remaining out of the pressed bar.

Other techniques, in addition to casting and pressing, may be used to form the anode 6.

An alternative embodiment is the bismuth anodes 6 are fabricated with the nickel wire wrapped tightly around the anode 6, cast form or pressed form, with 3 inches of unwrapped wire 12.

An alternative exemplary embodiment comprises a manufacturing of a cell 100 with an anode 6 of pure bismuth fabricated where the cathode assembly 5 and diffusion membrane 3 are assembled into the outer housing 1 of the cell. Further per the embodiment the gas permeable diffusion membrane 3 is made of a Teflon® thin film of approximately 25 microns in thickness and the cathode assembly 5 is comprised of a gold catalyst 202 deposited 60 to 100 nanometers thick on the diffusion membrane 5 through deposition techniques such as sputtering, a carbon fiber 203 that may be formed in a sheet approximately 1 millimeter thick, a metal retaining disk 204 screen approximately 1 millimeter thick with holes in the screen 204 of approximately a 1 millimeter square area as referenced in FIG. 2 where the metal retaining screen 204 is of titanium or stainless steel, with a gold coated plated titanium cathode electrical lead wire 8 approximately 0.020 inch diameter. A cathode 5 and diffusion membrane retainer component 2 with a nitrile O-ring 10 assembled and bonded with a cyanoacrylate adhesive to the outer cell housing 1 to secure the cathode 5 and diffusion membrane 3 assemblies in place. As per the embodiment the bismuth anode 6 is assembled inside the outer cell housing 1 and the outer cell housing containment base plate 1a that is assembled and coupled to the outer housing 1. The nickel wire lead 12 extending out of the housing 1 and assembled to the electronic circuit board 7. The housing materials 1 and all plastic housing components for the cell 100 may be made of chlorinated polyvinyl chloride plastic due to its chemical resistance required for cells in applications with exposure caustic gasses. The electrolyte 4 comprised of aqueous potassium hydroxide (KOH) or aqueous acetic acid (CH3COOH), two common electrolytes 4 in the field of electrochemical cells, is dispensed inside the cavity of the cell housing 100 and the cell housing 100 is sealed with a chlorinated polyvinyl chloride plastic plug 13. This restricts the flow of oxygen through the diffusion membrane 3 into the cell 100 for the electrochemical process. The anode 6 and the cathode electrical lead wires 8, 12 are soldered to the circuit board 7 and electrical leads 9 which comprise a resister and thermistor to convert the microamperes (μA) current generated by the electrochemical process to a voltage output, in certain embodiments may be in the millivolt (mV) range required by current instrumentation and devices in industry. The mV output range per certain embodiments has a linear proportional relationship to the percentage of O2 in the gas sample or environment being measured. An end cap 11 is bonded to the back of the cell 100 to enclose and protect the circuit board 7.

Another exemplary embodiment comprises the construction of the diffusion membrane 3 and cathode assembly 5 as further described and referenced in FIG. 2. Per the exemplary embodiment the diffusion membrane assembly 3 is comprised of a fluorinated polymer film 1 or a gas permeable film with oxygen diffusion properties and rates of approximately $1.72 \times 10^{-13}$ moles per second at 100% oxygen exposure or alternatively per the embodiment $6.48 \times 10^{-11}$ moles per second at 21% oxygen exposure. Alternative rates would be acceptable per the required embodied application use specifications. The cathode assembly 5 is comprised of a carbon fiber sheet material 203 of approximately 1 millimeter thickness. A gold film 2 of 60-100 nanometers is deposited on the carbon fiber 203 sheet. Such deposition per the embodiment is performed by Magnetron Sputtering or other physical deposition techniques comprising but not limited to pulsed laser deposition, spin coating, evaporation deposition and chemical vapor deposition. The deposition of the gold 202 on the carbon fiber 203 provides for an increase of three phase boundaries oxygen reduction sites which results in a higher amperage output signal. The gold sputtered cathode assembly 5 is secured by the metal retaining screen 204 and connected to the electrical circuit 7 of the cell 100 with a gold plated titanium wire 8 as per the embodiment and as referenced in FIG. 1.

Further alternate exemplary embodiment in construction of the diffusion membrane 3 also referenced in FIG. 1, and cathode assembly 5 is to deposit the gold 202 on the diffusion membrane 3 and assemble a non-gold coated carbon fiber substrate 203 such as a sheet between the gold layer 202 of the diffusion membrane 3 and the metal retaining screen 204.

Figure 5:
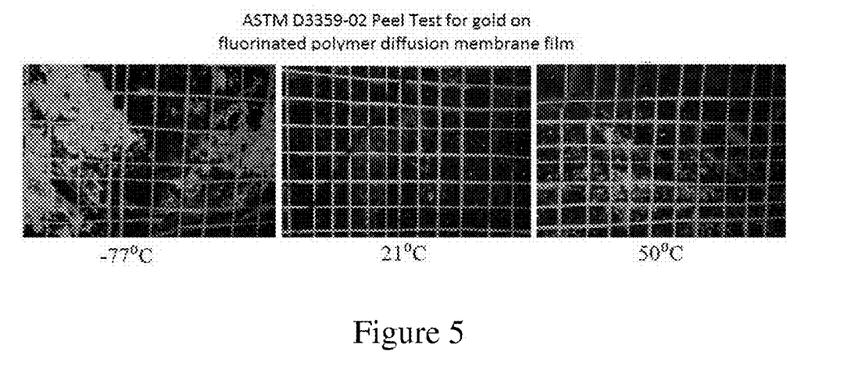
FIG. 5 shows imaging of adhesion peel test results for Gold Film to the Fluorinated Polymer Diffusion Membrane.

Another exemplary embodiment is the process of the physical deposition of the gold 202 to the fluorinated polymer diffusion membrane film 3. Per the embodiment using Magnetron sputtering deposition techniques, the material stage and diffusion material demonstrated best adhesion properties with the gold thin film layers 202 when controlled at 21 degrees centigrade as shown in FIG. 5.

Exemplary to the embodiment thereof is the characterization of the cell 100 using cyclic voltammetry showing linearity. The cell 100 as detailed above in the embodiment with the two alternative embodiment electrolyte solutions 4, potassium hydroxide (KOH) and acetic acid (CH3COOH), the embodied anodes 6, cast and pressed bismuth and a gold 202 sputtered fluorinated polymer film 3, Fluorinated Ethylene Propylene, cathode 5. The working potential was applied in the standard way using the Gamry Reference 600TM Potentiostat/Galvanostat/ZRA device and the output signal was acquired and analyzed with the Gamry eChemDC and eChemAC software.

Exemplary to the embodiment, all chemicals and materials were of analytical reagent grade and were able to be used without any additional purifying or processing.

Per the embodiment potassium hydroxide (KOH) electrolyte 4 was made with highly pure distilled water and fully dissolved potassium hydroxide (KOH) pellets. The electrolyte 4 was made by blending 0.9268 grams of potassium hydroxide (KOH) pellet with 0.2317 grams of DI H2O for every milliliter (ml) of electrolyte to make a 20% potassium hydroxide (KOH) solution 4.

Alternatively per the embodiment, acetic acid (CH3COOH) electrolyte 4 is formulated with highly pure distilled water, potassium acetate and glacial acetic acid (CH3COOH) to make a 6.0 molar aqueous solution 4.

Alternative to the embodiment is the use of a solid electrolyte 4 material in the cell.

Figure 3:
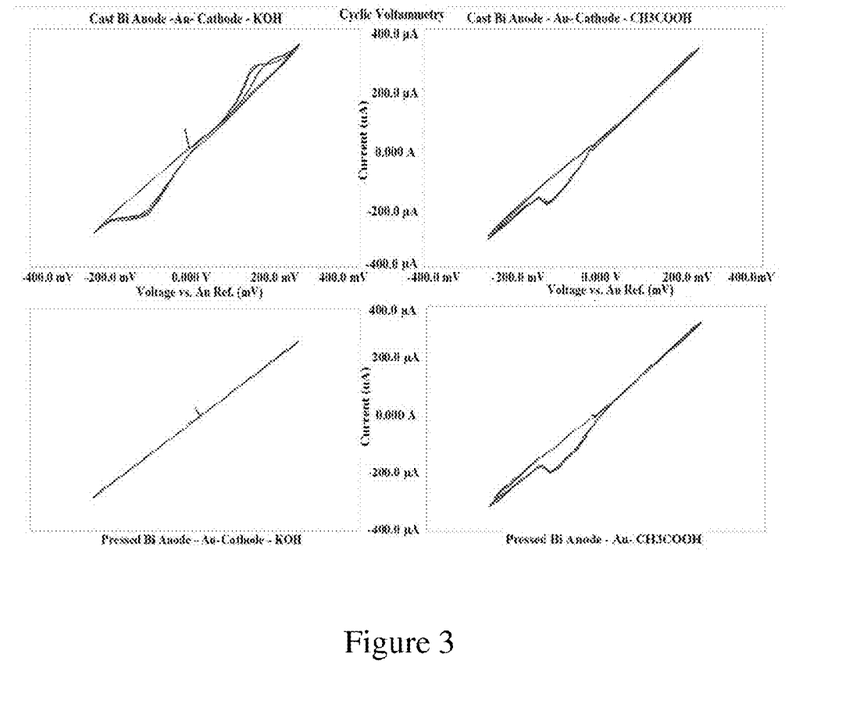
FIG. 3 graphically shows Cyclic Voltammetry Characterizations.

FIG. 3 shows the exemplary embodiment results of cyclic voltammetry testing. When an applied voltage in the range of a typical current cell 100 in industry is applied, the current output relation is dominantly linear as desired.

Figure 4:
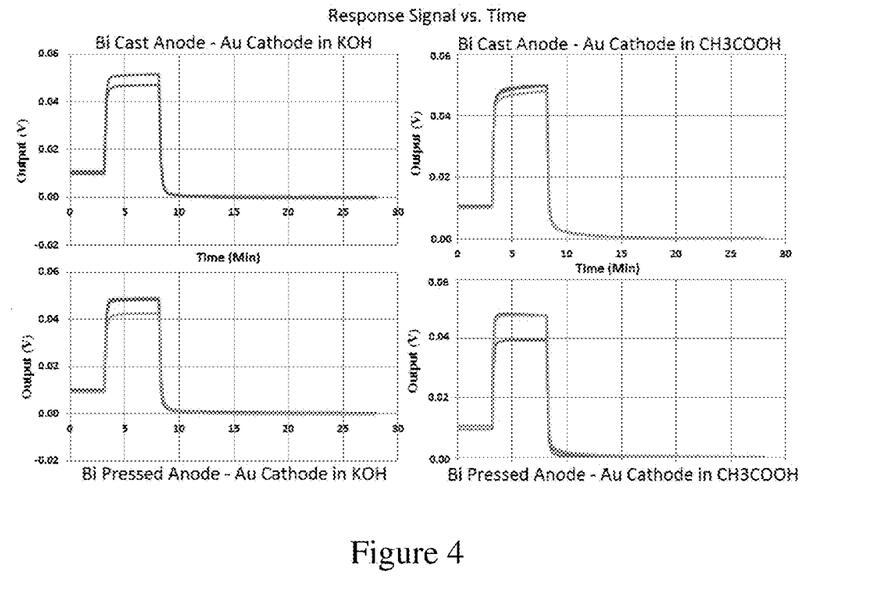
FIG. 4 graphically shows Response Signal vs. Time and oxygen percentage using different techniques for forming the anode.

Further to the exemplary embodiment, the response time and electrical output per the percentage of oxygen are a requirement for a cell 100 in various industry applications. FIG. 4 references cells 100 per the embodiment with the cast and pressed Bismuth anode 6 respectively with a gold 202 cathode 5 tested per by exposure to various levels of oxygen in accordance to BS EN ISO 21647:2009 for medical device oxygen monitors with electrochemical oxygen cells 100. These levels of oxygen percentage are 0%, 21%, and 100%. Exemplary to the embodiment is the satisfactory results referenced in FIG. 4 for the response time and the stabilization time from the defined standard for said devices, BS EN ISO 21647:2009.

One exemplary embodiment is the testing of the cells 100 per the embodiment with an automated testing apparatus. The apparatus is comprised of circuit boards designed with Delrin™ fixtures for cell seating, attachment cables, gas tubing with a solenoid gas switching bus, a SCXI-1000 Chassis with SCXI-1100 multiplexors, a PC computer with LabView software and a NI PCI-6040E DAQ card. This system is connected to three gas cylinders containing 100% oxygen, 20.9% oxygen/79.9% nitrogen, and 0% oxygen/100% nitrogen respectively.

Although specific embodiments and applications of the invention have been described in this specification, these embodiments and applications are exemplary only, and many variations are possible.

I claim:

1. An electrochemical oxygen sensor comprising:
an electrochemical cell, the electrochemical cell further comprising:
a solid anode comprising at least 99.997% bismuth;
a cathode assembly comprising a cathode and a diffusion membrane, the diffusion membrane contacting the cathode on a face, the diffusion membrane contacting an environment on another face, the diffusion membrane configured to be permeable to oxygen gas;
a container configured to contain the electrochemical cell and an O-ring configured to secure the diffusion membrane to the container; and
an electrolyte configured to contact the anode and the cathode assembly;
wherein oxygen gas diffusing across the diffusion membrane from the environment to the cathode generates a current directly proportional to a percentage of oxygen gas in the environment;
wherein the O-ring contacts the diffusion membrane to prevent electrolyte from leaking from the electrochemical cell and to stretch the diffusion membrane to promote consistent and constant diffusion of oxygen gas across the diffusion membrane;
wherein the cathode assembly further comprises a cathode comprising a gold film deposited on one side of a carbon fiber sheet and a perforated metal retaining screen disk configured to secure the carbon fiber sheet on another side.

2. The sensor of claim 1, further comprising an electronic circuit board configured to measure the current generated.

3. The sensor of claim 1, further comprising an resistive circuit board configured to convert the current to a voltage output.

4. The sensor of claim 1, wherein the sensor is RoHS compliant.

5. The sensor of claim 1, wherein the diffusion membrane further comprises a fluorinated polymer film.

6. The sensor of claim 1, wherein the diffusion membrane further comprises polytetrafluoroethylene.

7. The sensor of claim 1, wherein the diffusion membrane has a thickness of about 25 microns.

8. The sensor of claim 1, wherein the electrolyte further comprises potassium hydroxide.

9. The sensor of claim 1, wherein the electrolyte further comprises acetic acid.

10. The sensor of claim 1, wherein the cathode further comprises gold or platinum.

11. The sensor of claim 1, wherein the gold film is deposited on one side of the carbon fiber sheet by magnetron sputtering.

12. The sensor of claim 1, wherein the gold film has a thickness of between about 60 nanometers and 100 nanometers.

13. The sensor of claim 1, wherein the carbon fiber sheet has a thickness of about 1 millimeter.

14. The sensor of claim 1, wherein the cathode comprises a metal layer deposited on a side of the diffusion membrane closest to the electrolyte.

15. An electrochemical oxygen sensor comprising:
a container comprising a chemically resistant material;
an electrochemical cell contained within the container, the electrochemical cell further comprising:
a solid anode comprising at least 99.997% bismuth;
a cathode assembly comprising a cathode, a diffusion membrane configured to be permeable to oxygen gas, and an O-ring configured to secure the diffusion membrane to the container; and
an electrolyte configured to contact the anode and the cathode assembly;
wherein the diffusion membrane contacts the cathode on a face and contacts an environment on another face;
wherein oxygen gas diffusing across the diffusion membrane from the environment to the cathode generates a current directly proportional to a percentage of oxygen gas in the environment;
wherein the O-ring contacts the diffusion membrane to prevent electrolyte from leaking from the electrochemical cell and to stretch the diffusion membrane to promote consistent and constant diffusion of oxygen gas across the diffusion membrane;
wherein the cathode assembly further comprises a cathode comprising a gold film deposited on one side of a carbon fiber sheet and a perforated metal retaining screen disk configured to secure the carbon fiber sheet on another side.

16. The sensor of claim 15, further comprising an electronic circuit board configured to measure the current generated.

17. The sensor of claim 15, wherein the gold film is deposited on one side of the carbon fiber sheet by magnetron sputtering.

18. The sensor of claim 15, wherein the gold film has a thickness of between about 60 nanometers and 100 nanometers.

19. The sensor of claim 15, wherein the carbon fiber sheet has a thickness of about 1 millimeter.

* * * * *

UNITED STATES PATENT AND TRADEMARK OFFICE
CERTIFICATE OF CORRECTION

PATENT NO. : 9,146,208 B2  
APPLICATION NO. : 13/630550  
DATED : September 29, 2015  
INVENTOR(S) : Alan Boardman Page 1 of 1

It is certified that error appears in the above-identified patent and that said Letters Patent is hereby corrected as shown below:

In the claims

Claim 1 at Column 8 and lines 4-5 which reads "wherein the cathode assembly further comprises a cathode comprising" should read --wherein the cathode further comprises--.

Claim 15 at Column 8 and lines 63-64 which reads "wherein the cathode assembly further comprises a cathode comprising" should read --wherein the cathode further comprises--.

Signed and Sealed this
Twelfth Day of April, 2016

Michelle K. Lee
*Director of the United States Patent and Trademark Office*